US010736595B2

United States Patent
DiNitto

(10) Patent No.: US 10,736,595 B2
(45) Date of Patent: Aug. 11, 2020

(54) SKULL PIN ARTIFACT ROTATION FOR THE USE IN IMAGE-GUIDED NEUROSURGERY PROCEDURES

(71) Applicant: Siemens Medical Solutions USA, Inc., Malvern, PA (US)

(72) Inventor: Julie DiNitto, Memphis, TN (US)

(73) Assignee: Siemens Healthcare GmbH, Erlangen (DE)

( * ) Notice: Subject to any disclaimer, the term of this patent is extended or adjusted under 35 U.S.C. 154(b) by 205 days.

(21) Appl. No.: 15/907,517

(22) Filed: Feb. 28, 2018

(65) Prior Publication Data

US 2018/0249980 A1   Sep. 6, 2018

Related U.S. Application Data

(60) Provisional application No. 62/466,986, filed on Mar. 3, 2017.

(51) Int. Cl.

| | |
|---|---|
| *A61B 6/00* | (2006.01) |
| *A61B 6/03* | (2006.01) |
| *A61B 6/04* | (2006.01) |
| *A61B 6/12* | (2006.01) |

(52) U.S. Cl.
CPC ............ *A61B 6/5258* (2013.01); *A61B 6/032* (2013.01); *A61B 6/0421* (2013.01); *A61B 6/0457* (2013.01); *A61B 6/12* (2013.01); *A61B 6/4085* (2013.01); *A61B 6/4441* (2013.01); *A61B 6/469* (2013.01); *A61B 6/501* (2013.01); *A61B 6/465* (2013.01); *A61B 6/466* (2013.01); *A61B 6/545* (2013.01)

(58) Field of Classification Search
None
See application file for complete search history.

(56) References Cited

U.S. PATENT DOCUMENTS

2013/0190604 A1\* 7/2013 Moffatt ............... A61B 5/0555
600/411
2017/0273654 A1\* 9/2017 Taguchi ............... A61B 6/5258
2018/0028127 A1\* 2/2018 Litzenberger .......... A61B 6/548

\* cited by examiner

*Primary Examiner* — Hoon K Song

(57) ABSTRACT

An image control system has a table, a head frame, an imaging system, a rotation system, and a control system. The head frame includes at least one pin which immobilizes a select patient anatomy with respect to the table while the imaging system collects image data through a CT scan process. The CT scan process produces an image of the patient anatomy, with the image including an artifact associated with the at least one pin. The artifact masks an area of interest in the image. The control system determines an angle of rotation which will move the artifact out of the area of interest and rotates at least one of the table, the head frame, and the imaging system by the angle of rotation. A subsequent image produced by the CT scan process includes an image of the patient anatomy with the artifact moved out of the area of interest.

20 Claims, 7 Drawing Sheets

SKULL PIN ARTIFACT ROTATION FOR THE USE IN IMAGE-GUIDED NEUROSURGERY PROCEDURES

CROSS-REFERENCE TO RELATED APPLICATIONS

This application claims the benefit of U.S. Provisional Application Ser. No. 62/466,986 filed Mar. 3, 2017, which is incorporated herein by reference in its entirety.

TECHNICAL FIELD

The present invention relates generally to image-guided neurosurgery procedures, and, more particularly, to performing artifact rotation in neurosurgery procedures to produce an unobstructed image and measuring the physical angle of rotation needed for producing the unobstructed image.

BACKGROUND

Neurosurgical procedures, at times, will require imaging and immobilization of the head simultaneously. The immobilization of the head is maintained by a head frame that attaches to the head using pins, typically made of titanium. Titanium is the most common choice because it is cost effective, biocompatible, and fracture resistant. Regardless of the many excellent qualities of titanium, titanium has a high density which creates very large and dense artifacts in its x-ray trajectory path. These artifacts can cause masking of important information and reduce visualization of critical anatomy.

Earlier attempts to resolve these artifacts include measures of re-attachment of the head frame, prior image fusion, or by ignoring the issue with no solution and continuing on with the procedure. These solutions are not ideal as they introduce unnecessary risk of injury to the patient and risk of missing a potentially important aspect of an image. Another solution is the replacement of titanium with carbon fiber or sapphire pins, but this comes at a great expense. The present disclosure describes a procedure to redirect artifacts caused by titanium skull pins in order to overcome the problems described above in an efficient and cost-effective manner.

SUMMARY

Embodiments of the present invention address and overcome one or more of the above shortcomings and drawbacks, by providing methods, systems, and apparatuses related to artifact rotation in neurosurgery procedures to produce an unobstructed treatment area image and measuring the physical angle of rotation needed for producing the unobstructed image.

According to some embodiments, the present disclosure is directed to a computer-implemented method for producing an image of a patient anatomy using x ray through an image control system. The method includes receiving image data associated with a CT scan of the patient anatomy while the patient anatomy is immobilized by one or more pins and receiving identification of a location of an area of interest which is masked by an artifact associated with the one or more pins. The method further includes identifying, by a processor, an angle of rotation which will rotate the artifact out of the area of interest. The method also includes receiving second image data associated with a second CT scan of the patient anatomy after a component of the image control system is rotated by the identified angle of rotation, and producing an image of the patient anatomy with the artifact moved out of the area of interest.

According to other embodiments, the present disclosure is directed to an image control system. The image control system includes a table including a surface for supporting a patient, a head frame including at least one pin configured to be secured to a patient anatomy in order to immobilize the patient anatomy relative to the table, and an imaging system configured to perform a CT scan in order to produce an image of the patient anatomy using x-rays. The image control system further includes a rotation system configured to rotate the at least one pin relative to a path of the x-rays in order to adjust or alter a position of an artifact associated with the at least one pin in a subsequent image of the patient anatomy.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

Many neurosurgical procedures utilize an immobilization system which helps to protect the patient by keeping the patient's skull still on the table. The immobilization system may typically include skull pins or screws which attach at different points of the skull. The immobilization of the skull protects the patient during a subsequent procedure by limiting movement. While immobilized, an imaging procedure may be performed to scan the patient's head and obtain various images which will help plan and guide the neurosurgical procedure.

Figure 1:
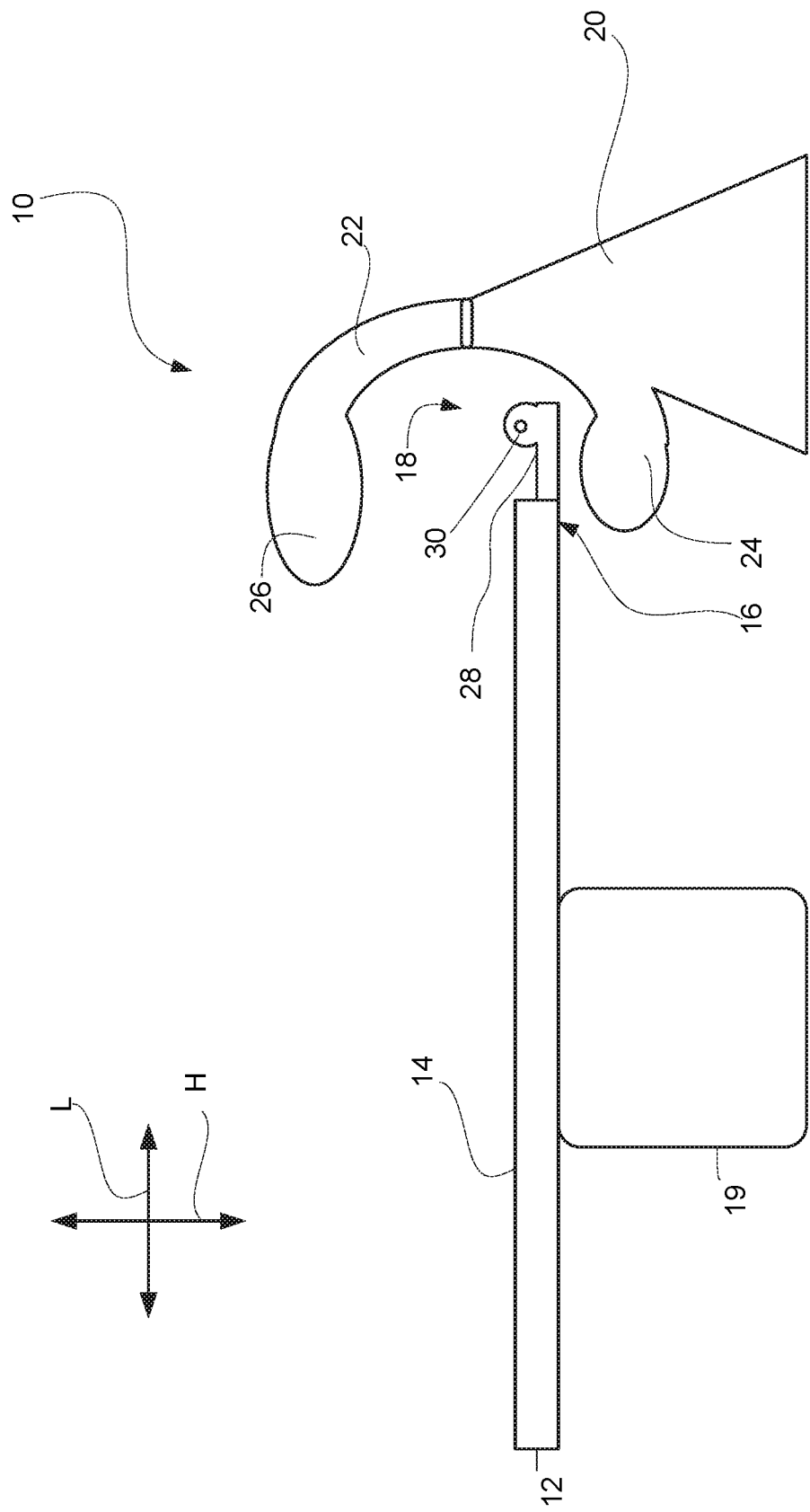
FIG. 1 is a side view of a system for immobilizing and imaging a skull of a patient.

FIG. 1 illustrates an example of an immobilization and imaging system 10 which includes a table 12 for supporting a patient on a surface 14. The table 12 extends in a length direction L in a horizontal plane which is parallel to the plane of the page of FIG. 1. A height direction H is perpendicular to the length direction L. The table 12 includes an end 16 at which the patient positions their head. The immobilization and imaging system 10 further includes a head frame 18 at the end 16 of the table 12. The head frame 18 is preferably attached to the table 12. In some embodiments, the table 12 further includes a base 19 which supports the table 12 and positions the surface 14 at an appropriate height. The base 19 may include a rotation mechanism which allows the table 12 to rotate, as will be described in more detail.

The head frame 18 includes components which fixedly attach the patient to the table. For example, the head frame 18 may include a clamp mechanism 28 and an attachment mechanism 30. The clamp mechanism 28 includes connection components which connect a body of the head frame 18 to the table 12. The attachment mechanism 30 includes features which connect the body of the head frame 18 to the patient. In an exemplary embodiment, the attachment mechanism 30 includes pins, preferably made of titanium. The pins are attached to the patient's skull in a manner known in the art, thereby immobilizing the patient's head with respect to the table 12. The term "pin" is used herein to describe an elongated element which attaches to the skull and encompasses elements such as screws, nails, bolts, etc.

The immobilization and imaging system 10 further includes an imaging system 20 which is configured to scan the patient's head area and produce images of a target area (e.g., skull, brain, etc.). In an exemplary embodiment, the imaging system 20 preferably includes a flat panel computed tomography (CT) system which utilizes x-ray imaging in order to obtain images of an internal body structure, such as that within the patient's skull. However, it should be understood that other types of x-ray systems may be used.

As shown in FIG. 1, the imaging system 20 may include a C-arm 22 which is positioned adjacent to the table 12 and which includes a detecting element 24 and a transmission element 26 positioned across from the detecting element 24. The detecting element 24 produces x-rays which travel through the target area of the patient and are received at the transmission element 26. The imaging system 20 further includes processing components which are configured to output measurements and images as a result of the x-ray procedure.

As is known in the art, the C-arm 22 is configured to rotate about an axis to capture 2-D projection images at incremental angles around the circumference of the patient's skull. The rotational axis is parallel to the length direction of the table 12 when the table 12 is in a perpendicular orientation. The physical rotation of the C-arm 22 moves the detecting element 24 and the transmission element 26 around the table, with the detecting element 24 and transmission element 26 maintaining the same opposing relative position as they travel around the table 12. The imaging system 20 is configured to output a measurement on imaging through the use of CT at various angles around the table 12. For example, the imaging system 20 may utilize cone beam CT flat panel detection (such as the Siemens Artis Zeego system, produced by Siemens Healthcare, Forchhiem, Germany). The measurements may include, for example, 109 kV Dyna CT, Large Volume Dyna CT, and/or 360° Dyna CT analysis. The rotation of the imaging system 20 produces a set of images at different angles which can be compiled by the processing components of the imaging system 20 into a 3-D model of the patient's head, as is known in the art. The imaging system 20 allows a practitioner to explore the 3-D model to view the patient's skull and brain at varying angles and planes of view as reconstructed 2-D images of the 3-D model.

Figure 2:
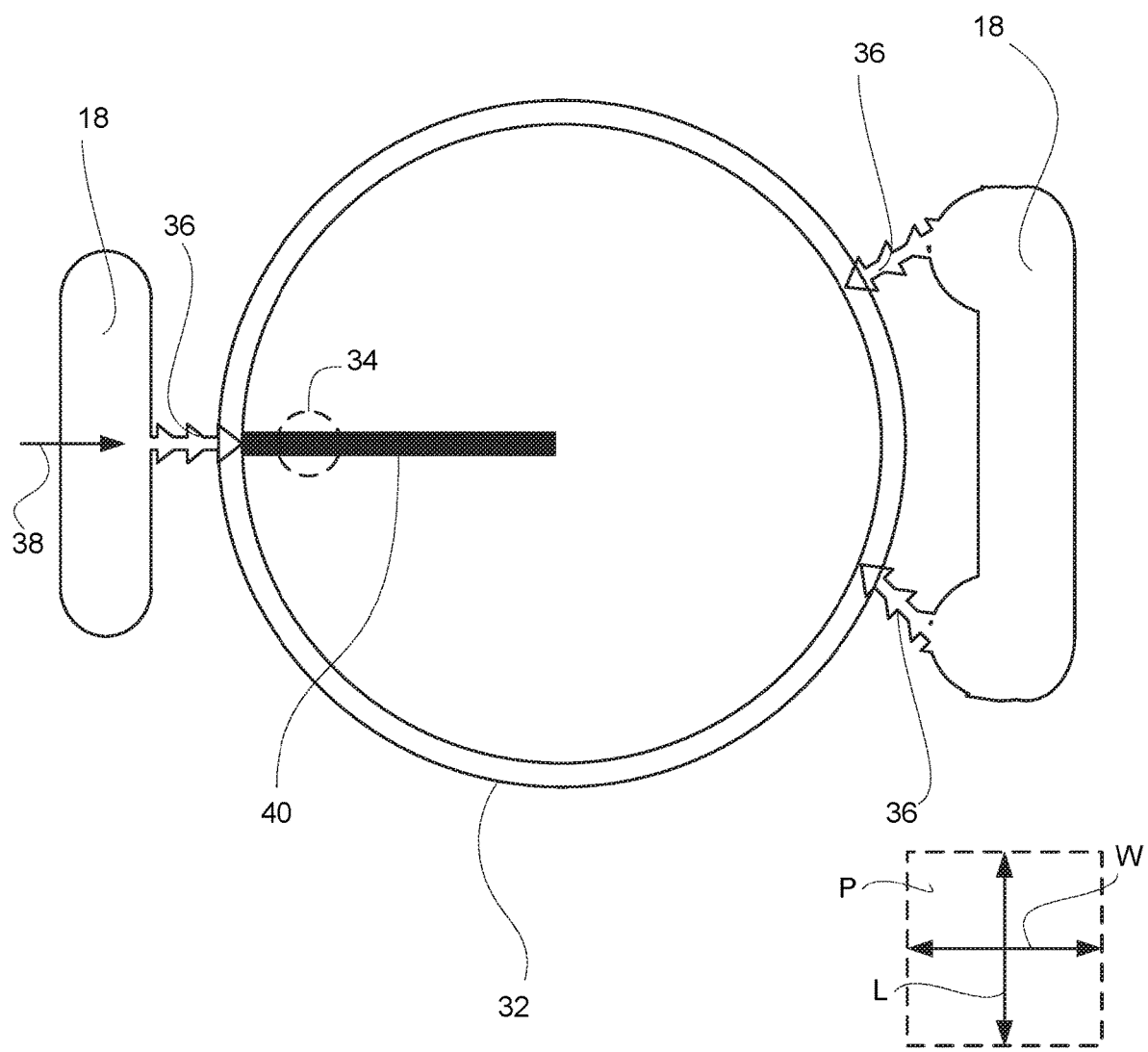
FIG. 2 is a schematic diagram of a reconstructed 2-D image of a patient skull which is immobilized though the use of titanium pins.

FIG. 2 is a schematic diagram of one such reconstructed 2-D image which further illustrates components of the immobilization and imaging system 10 as well as an example of a patient's cranial structure. The diagram of FIG. 2 is essentially a top-view of the patient, in a plane P which is parallel to the plane of the table 12. FIG. 2 illustrates schematically a patient's skull 32. Within the image is also an area of interest 34, which corresponds to a location within the image which may or may not include information which is needed for the treatment of the patient. The area of interest 34 could be located anywhere within the 3-D model produced by the imaging system 20, and thus may be present in any of a number of reconstructed 2-D images produced from the 3-D model.

As the diagram is that of an reconstructed 2-D image that may be produced by the imaging system 20, it further includes pins 36 of the head frame 18, as these elements show up in 2-D projection images of the CT scan. The pins 36 are placed at various locations and attached to the skull 32 in order to complete immobilization of the patient's head with respect to the table 12. In one example, the pins 36 extend longitudinally in the plane P parallel to the table, although it should be understood that the pins 36 could potentially extend in other planes. In the embodiment shown, one of the pins 36 travels on a trajectory path 38 which is in the width direction W.

In this example, it is assumed that the pins 36 are formed from titanium; however, it should be understood that other materials with similar properties may be used in other embodiments of the present invention. The pins 36 produce an artifact 40 which shows up in the reconstructed 2-D image which is produced from the 3-D model generated by the imaging system 20. The artifact 40 is a feature in the image which is a misrepresentation of the underlying structure being imaged, such as an area which is erroneously presented as a darkened area in the reconstructed 2-D image.

The artifact 40, according to an exemplary embodiment, is produced as a result of the high density of titanium and the resulting effect on an x-ray image, in addition to the manner in which the image is produced. As the C-arm 22 rotates, the imaging system 20 will capture x-ray measurements which travel through the pins 36, including instances in which the x-rays travel directly through the longitudinal direction of the pins 36 (i.e., the trajectory path 38 when the detecting element 24 and transmission element 26 are positioned across from each other in the plane P). In these images, the titanium pins block the x-rays along their longitudinal trajectory path 38, causing the imaging system 20 to miss information on this path due to x-ray absorption. When the processing device of the imaging system 20 combines the various incremental 2-D projected images into a 3-D model, the artifact 40 is displayed in areas which should display skull internal anatomy. This characteristic of x-ray imaging thereby presents a potential problem for the practitioner, as it is possible that the artifact 40 is masking important patient anatomy which is needed for evaluating the patient and/or guiding a subsequent neurosurgical procedure. For example, the artifact 40 may hide a feature such as a tumor or abnormality which is critical to the treatment of the patient. While one artifact 40 is illustrated in the diagram of FIG. 2, it should be understood that multiple artifacts may be present in a particular reconstructed 2-D image, such as artifacts associated with each of the multiple pins 36 along their respective longitudinal trajectory paths.

Consistent with disclosed embodiments, the immobilization and imaging system 10 includes features which are configured to address and ameliorate the effects of the artifact 40 such that important anatomical information is not missed in the CT images produced by the imaging system 20.

Figure 3:
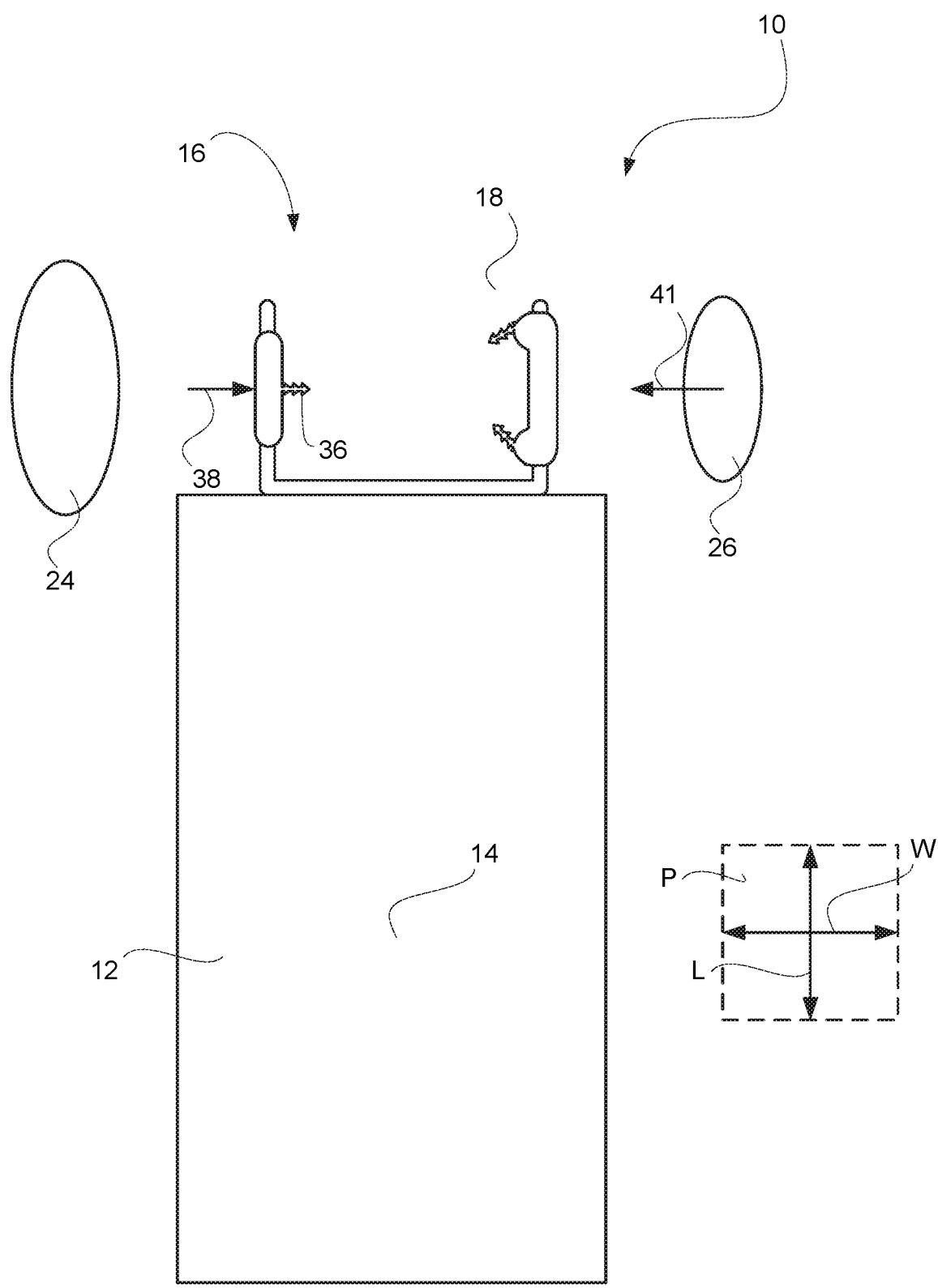
FIG. 3 is a top view schematic diagram of a table and scan system in a perpendicular orientation.

FIG. 3 is a schematic diagram of the immobilization and imaging system 10, including the table 12, the head frame 18, and the imaging system 20, including the detecting element 24 and the transmission element 26 in the plane P. FIG. 3 illustrates the current practice of the C-arm 22 being programmed to remain perpendicular to the table 12. In particular, a width direction W which is perpendicular to the longitudinal length L of the table 12, remains perpendicular to the axis of rotation of the C-arm 22.

However, the configuration of FIG. 3, in which the straight-line direction between the detecting element 24 and the transmission element 26 is parallel to the width direction W, regularly causes an x-ray trajectory 41 through the longest path length of one of the head frame pins 36, thereby producing a large artifact 40. In other words, the pins 36, which may generally or primarily extend along trajectory path 38, blocks much of the x-rays when a corresponding 2-D projection image is taken along the trajectory 41 because of the matching of the paths. This results in a high density trajectory path producing the artifact 40 which may mask an important feature of internal anatomy. While the paths 38, 41 are shown as being parallel to the width direction W, it should be understood that this is exemplary. In many instances, x-ray paths will be angled with respect to the width direction W, such as in cone beam CT scans. These angled paths may match with angled pins 36, thereby creating a large artifact similar to the artifact 40 illustrated in the figures.

By allowing a small freedom of rotation in the table 12 while remaining in the same length-width plane P, the x-ray path through the pins 36 can be altered and, in many cases, shortened. In alternative embodiments, the table may additionally or alternatively be capable of tilting with respect to the plane P, such as a rotation on a length or width axis. This configuration could provide an additional degree of freedom for the table, providing an additional option for changing the path of the pins 36. Changing the path of the pins 36 through which the x-rays travel will also change the path of the artifact 40.

Figure 4:
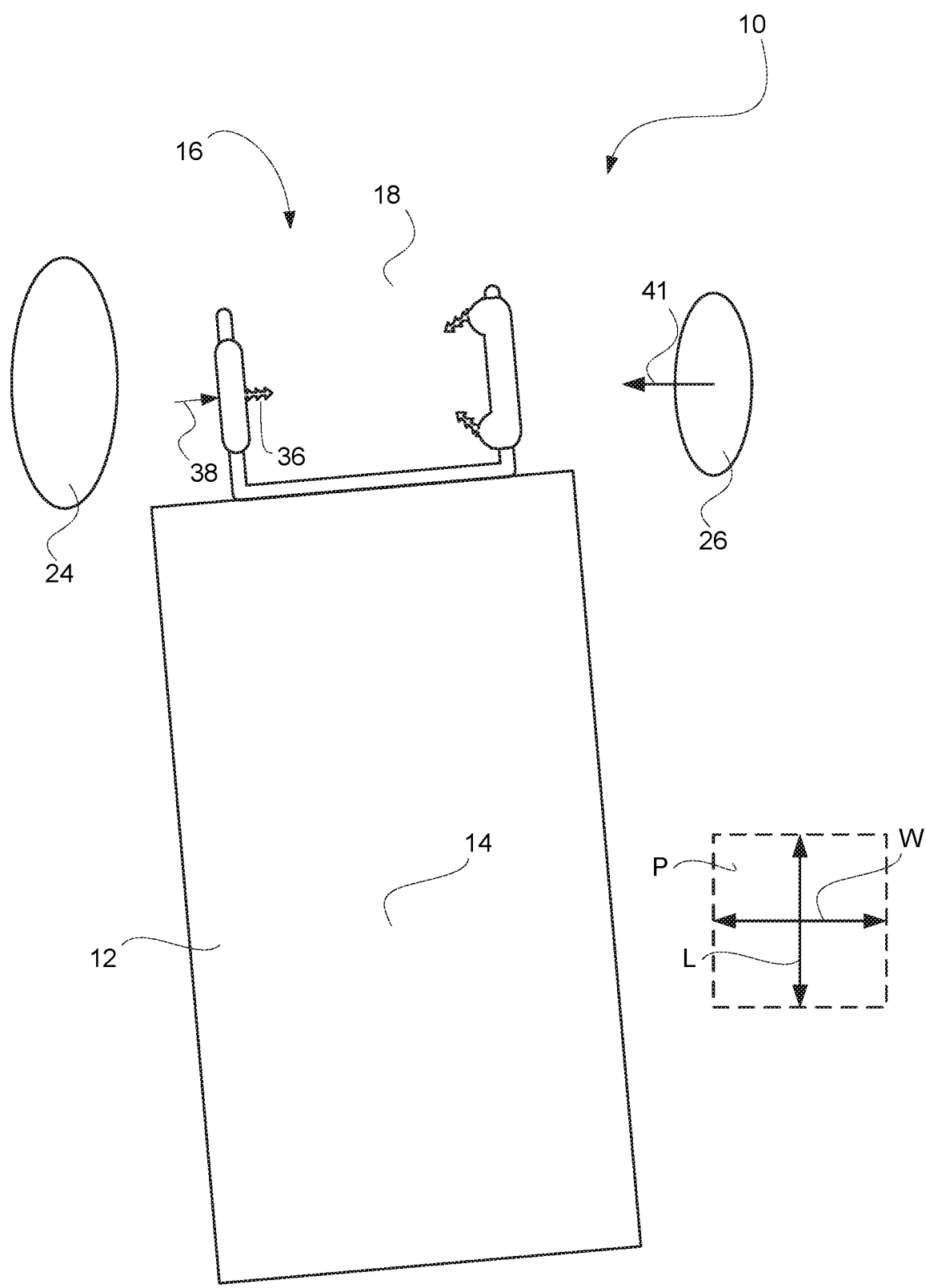
FIG. 4 is a top view schematic diagram of a table and scan system in a rotated orientation.

FIG. 4 illustrates an example of a table rotation consistent with disclosed embodiments. Even a small rotation such as this will move the artifact 40 and allow formerly masked portions of the images to be revealed. In addition, the movement of the patient is minimal to sufficiently rotate an artifact out of the region of interest. Artifacts that would otherwise obstruct important information can be redirected to a different angle and/or made smaller.

Figure 5:
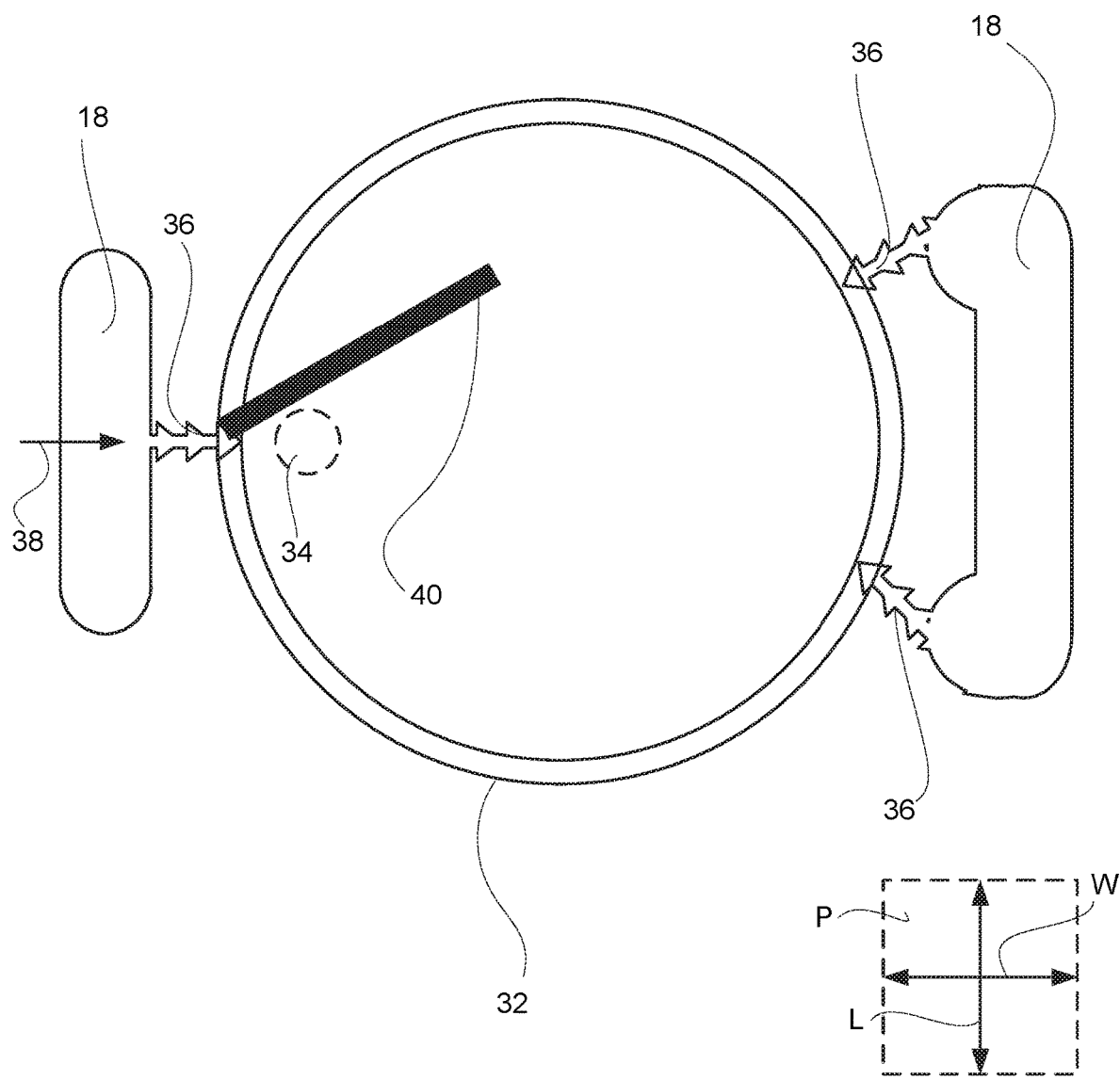
FIG. 5 is a schematic diagram of a reconstructed 2-D image including a rotated artifact.

FIG. 5 includes a schematic diagram of a reconstructed 2-D image which may be produced from a 3-D model generated by the imaging system 20 when the table 12 is moved to a rotated position. In the disclosed example, FIG. 2 is a diagram corresponding to a reconstructed 2-D image which may be produced by from a 3-D model generated by the imaging system 20 when the table 12 is in the position shown in FIG. 3, while FIG. 5 is a diagram corresponding to a reconstructed 2-D image which may be produced from a 3-D model generated by the imaging system 20 when the table 12 is in the rotated position of FIG. 4. The reconstructed 2-D images of FIGS. 2 and 5 are slices, at a selected angle, of the 3-D model which is produced by the imaging system 20.

FIG. 5 shows the artifact 40 has been rotated as a result of the rotation of the table 12. In particular, the x-ray path through the corresponding pin 36 was changed by rotating the table with respect to the detecting element 24 and the transmission element 26. While the table 12 is depicted as rotated in the exemplary embodiment, it should be understood that the table 12 needs only to be rotated with respect to x-ray paths to achieve a desired effect. This may be achieved by rotating the orientation of the detecting element 24 and transmission element 26 of the imaging system 20 or by rotating the head frame 18 and patient while keeping the table 12 still. In other words, the present embodiments include rotation of the pins 36 with respect to the x-ray paths, or vice versa, in some form.

The present disclosure includes systems and methods which utilize the feature of rotating the pins 36 with respect to the x-ray paths in order to adjust and/or alter the artifact 40 such that potentially critical anatomical regions are not masked in the images produced by the imaging system 20.

Figure 6:
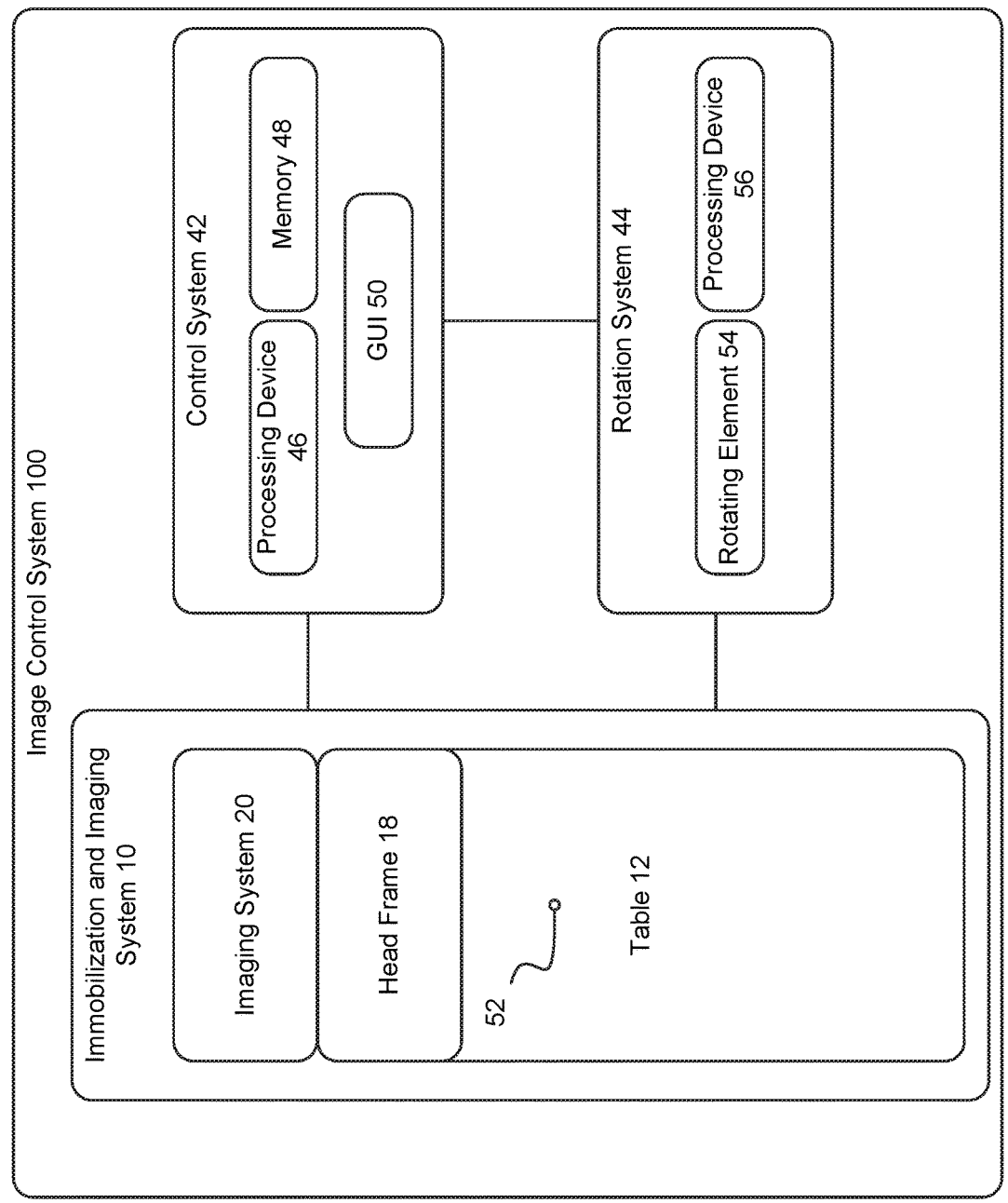
FIG. 6 is a system diagram illustrating components of a table control system.

FIG. 6 includes a system diagram which illustrates the components of an image control system 100 which may be utilized to implement the disclosed embodiments. The image control system 100 includes the immobilization and imaging system 10, a control system 42, and rotation system 44. The immobilization and imaging system 10 includes the table 12, head frame 18, imaging system 20, a pivot point 52. The pivot point 52 represents a point of relative rotation of one or more of the table 12, the head frame 18, and the imaging system 20. In one example, the pivot point 52 is located on the table 12 and allows the table 12 and the head frame 18 to rotate in the plane P with respect to the imaging system 20 (i.e., the x-ray paths of the imaging system 20). In another example, the pivot point 52 maybe located on the imaging system 20, allowing the detecting element 24 and the transmission element 26 to rotate in unison around the perimeter of the table in order to adjust the path of the x-rays with respect to the pins 36 of the head frame 18. For example, the C-arm 22 may be pivotable on a vertical axis to adjust the relative positioning of the detecting element 24 and the transmission element 26. In yet another example, the pivot point may be located on the head frame 18, such that the head frame 18, but not necessarily the table 12 rotates with respect to the imaging system 20 and the corresponding x-ray paths.

The control system 42 preferably includes a processing device 46, a memory 48, and an interface 50 (e.g., graphical user interface (GUI)). The processing device 46 may comprise one or more central processing units (CPU) and/or graphical processing units (GPUs). The control system 42 is connected to the imaging system 20 and is configured to received measurement data from the imaging system 20. The measurement data may include 3-D image data sufficient to produce a 3-D model or image of the cranial structure and associated anatomy. In some embodiments, the imaging system 20 may produce the compiled 3-D image, while the control system 42 may perform this analysis in other embodiments. In some embodiments, the control system 42 is a component of the imaging system 20. The control system 42 thus has access to the 3-D image data associated with multiple 2-D projection images captured by the imaging system 20.

The rotation system 44 includes a rotating element 54 and a processing device 56. The rotating element 54 is a mechanical element which is physically connected at the pivot point 52 and is configured to rotate the corresponding element, which may be the table 12, head frame 18, or imaging system 20. The rotating element 54 may include, for example, a motor which is configured to cause a rotation of the connected feature based on input from the processing device 56. The processing device 56 may comprise one or more central processing units (CPU) and/or graphical processing units (GPUs) The processing device 56 is electronically connected to the control system 42 and is configured to receive instructions from the control system 42, such as instructions to perform a rotation through the rotating element 54.

The image control system 100 addresses the problems posed by titanium pin artifacts by moving the artifacts 40 out of the way in order to reveal the underlying anatomy which may have been formerly masked by the artifact. The image control system 100 may execute one or more processes by which artifacts are rotated, thereby revealing underlying anatomy without having to remove and reattach the patient to and from the head frame 18. The image control system 100 is preferably configured to identify the amount of rotation necessary in order to reveal an area of interest, while taking into account various other factors that may affect the produced image. For example, by rotating to accommodate for one pin artifact, the path length through another pin may increase/decrease and cause an equal or lesser artifact from one of the other pins in the same plane.

The control system 42 is preferably configured with a system for measuring the trajectory of the pins 36 and determining the corresponding location of artifacts 40. In this way, the control system 42 is configured to identify a rotation angle which will result in a particular area being free from an artifact which mask an area of interest. For example, through use of CT imaging, the control system 42 is configured to physically measure the angle of rotation needed for a desired treatment planning step. Integrating this concept into practice will allow for reduction in re-attachment of head frames, reduce cost for head frame pins (instead of using alternative pins), and improve on visualization of region of interest for neurosurgical procedures.

In summary, by repositioning the pins 36 with respect to the x-ray path, such as by rotating the table 12, artifacts 40 are redirected and the image value improves for planning and overall treatment. The feature introducing rotation of the table 12 during 3D imaging acquisitions may require an additional amount of space (i.e., the virtual table becomes wider than the actual table and therefore limits the degrees off axis the table can move). This issue can be addressed by allowing rotation in both rotational directions (e.g., clockwise and counterclockwise).

Figure 7:
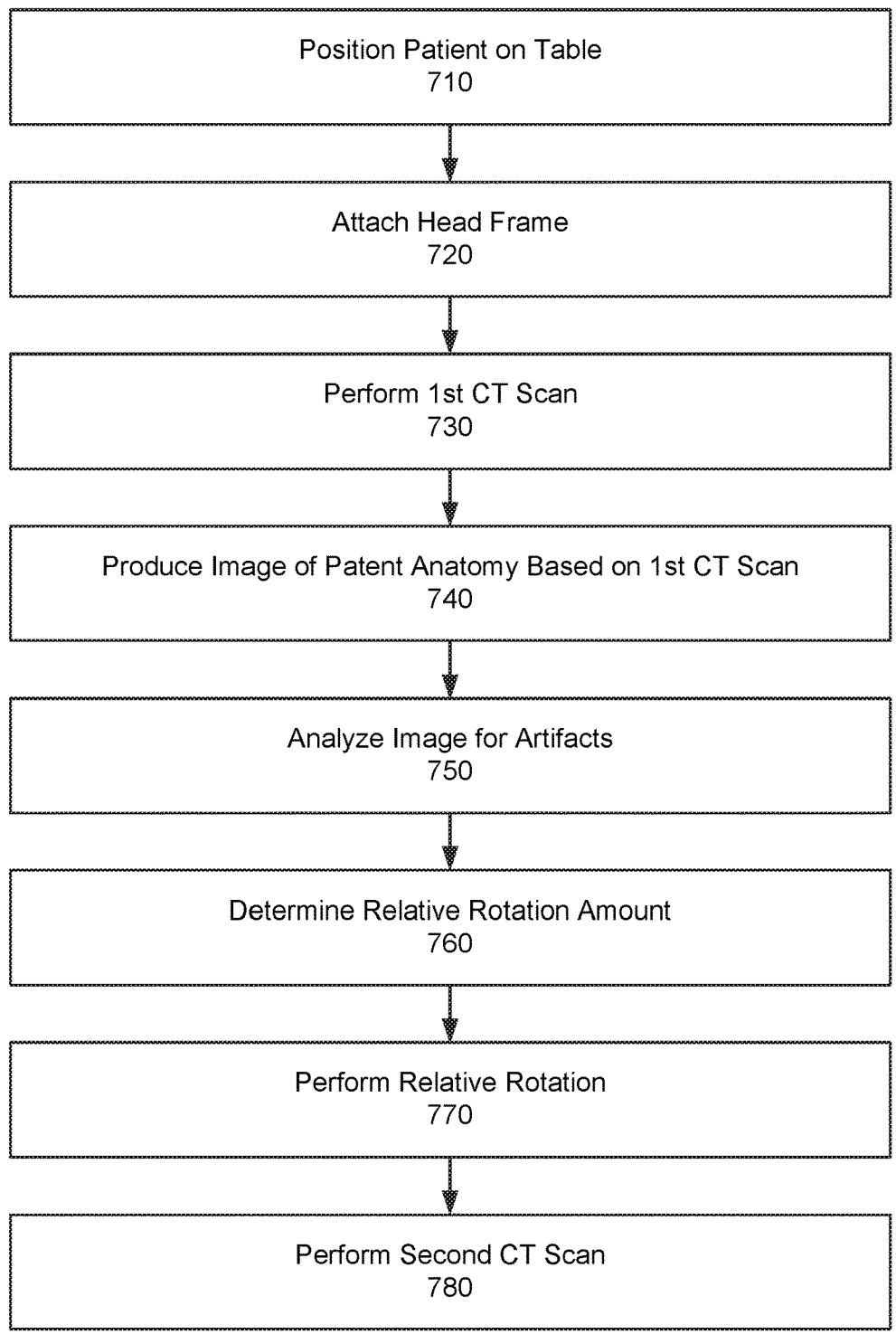
FIG. 7 is a flowchart of an exemplary process for planning a neurosurgical procedure which includes rotation of a table.

FIG. 7 includes a flowchart of an exemplary process 700 for obtaining desired images of a patient's cranial structure and associated anatomy through rotation of artifacts. The image control system 100 may execute at least some of the steps of the process 700 in order to produce the desired reconstructed 2-D images from the 3-D data. In step 710, the patient is positioned on the table 12. In step 720, the head frame 18 is attached. The pins 36 are attached to the skull such that the patient is secured in a stationary position relative to the table 12 and the head frame 18.

In step 730, the imaging system 20 captures 3-D data of the patient using the associated CT system of the C-arm 22, detecting element 24, and the transmission element 26, while in a perpendicular position (i.e., the position shown in FIG. 3). For example, the imaging system 20 may capture multiple 2-D projection images at varying locations around the patient's head while in the perpendicular position. In one embodiment, the imaging system 20 collects images at different angles around 360 degree circumference of the patient.

In step 740, the imaging system 20 produces an image or model of the patient's skull using the collected data. In one example, the imaging system 20 may produce a 3-D image using known methods, such as cone beam CT flat-panel detection. In step 750, the 3-D image is analyzed for artifacts. In one embodiment, this may include displaying the 3-D image on a GUI device and receiving input from a practitioner regarding the location of artifacts. In other embodiments, this may include the 3-D image data being provided to the control system 42 and the control system 42 analyzes the image data to identify the location of artifacts using 2D imaging in conjunction with provided 3D image data. For instance, a processing unit may identify the path of one or more pins 36 and use position data to identify the trajectory of the pin 36 in the images. In other embodiments, a processing unit may perform image analysis to identify artifacts.

In some instances, the artifacts will be positioned such that a least one area of interest is masked by an artifact in the images produced through step 740. As discussed throughout, this presents the potential issue of missing information which may be important or necessary to the practitioner in effectively treating the patient. For example, a site which will be addressed in a surgical procedure may be partially blocked, preventing the practitioner from having a clear view of the relevant area. In another example, a tumor or other abnormality may be missed or blocked by the artifact. The practitioner may manually identify these areas and provide input to the imaging system 20 or control system 42 through the GUI. In other embodiments, the imaging system 20 or control system 42 may identify these areas through an imaging analysis algorithm.

In step 760, the control system 42 identifies a relative rotation necessary to rotate or alter the artifact and reveal the underlying area in the images. For example, the control system 42 may receive the 3-D image data in addition to identification of a segmented area which is blocked by an artifact. The control system 42 is configured to determine an amount of relative rotation which will unmask the segmented area. The control system 42 may communicate with a memory or database and/or use a lookup table to determine an amount of rotation needed to reveal a particular area of interest, given the 3-D measurements. For example, the control system 42 may lookup particular rotations which correspond to an identified size and position of an artifact which are known to sufficiently move or alter the artifact.

In step 770, the relative rotation is carried out. In one embodiment, the relative rotation is achieved by rotating the table 12 with respect to the C-arm 22 of the imaging system 20. This could include, for example, a small rotation about a vertical axis while remaining in the same horizontal plane of the table which moves the pins 36 into a different trajectory path with respect to the x-rays emitted by the imaging system 20.

The rotation may be manual, semi-automatic, or fully automatic. In a manual embodiment, the control system 42 provides the rotation amount to a practitioner who operates the rotating element 54 in order to produce a rotation equal to the desired amount. In an automatic embodiment, the control system 42 provides the rotation amount to the rotation system 44 which may carry out the rotation through the rotating element 54. As described herein, the rotation may be applied to the table 12 directly. In other embodiments, the head frame 18 or C-arm 22 may be similarly rotated to adjust the positioning of the pins 36 with respect to the imaging system 20.

In step 780, a second 3-D scan is produced after the relevant rotation of the pins 36 is carried out. The second image capture scan is produced with the pins 36 rotated relative to the x-rays such that the resulting 3-D image will include the artifacts previously identified, in an altered or rotated state. The resulting 3-D image data can be used to produce a 3-D model from which various reconstructed 2-D images may be produced, such as the diagram of an image shown in FIG. 5. These images include unmasked areas which were previously covered by an artifact and thus include potentially important information that would have been missed in the original images.

Alternative embodiments may include additional or alternative features and are consistent with the present disclosure. In some embodiments the imaging system 20 may be configured to identify a necessary rotation without performing a current 3-D dimensional CT scan. Instead, a prior 3-D scan may be updated with a current 2-D image in order to update the previous image with the current location of the skull pins. This would avoid the need for two complete 3-D scans while the patient is connected to the head frame 18. In some embodiments, the image control system 100 may be configured to produce a composite image which includes minimal or no artifacts. That is, the two 3-D image data sets (prior to rotation and after rotation) may be combined and the artifacts canceled from the images in order to produce clean images which reveal all areas of interest. This feature would be particularly helpful when there are many areas of interest or a large area of interest such that rotation of the artifact alone cannot achieve a completely clear area of interest. Instead, the combination of two images with the artifact rotated in each image may provide a composite image which includes a clear area of interest.

The advantages of rotating the artifacts away from the region of interest include visualization being re-established for the procedure while still using cost effective titanium pins rather than costly alternatives such as sapphire or carbon fiber. In addition, the disclosed system relieves the patient from having the head frame re-attached at a different location and the practitioner from resorting to use previous images which may not accurately represent the current patient situation. Moreover, the treatment planning capable through the disclosed system could reduce the number of scans needed to proceed with the procedure and in return reduce radiation to the patient.

The embodiments of the present disclosure may be implemented with any combination of hardware and software. For example, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. For instance, while the disclosed embodiments describe immobilization and imaging of a patient's skull, it should be understood that this is one example and that the same aspects and features can be applied to other imaging procedures, such as imaging associated with other parts of the anatomy.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) unless the element is expressly recited using the phrase "means for."

The invention claimed is:

1. A computer-implemented method for producing an image of a patient anatomy using x-ray through an image control system, the method comprising:
    receiving image data associated with a CT scan of the patient anatomy while the patient anatomy is immobilized by one or more pins, the image data comprising an area of interest which is masked by an artifact associated with the one or more pins;
    determining, by a processor, a trajectory of the one or more pins based on the image data;
    identifying, by the processor, an angle of rotation which will rotate the artifact out of the area of interest based on the trajectory of the one or more pins;
    receiving second image data associated with a second CT scan of the patient anatomy after a component of the image control system is rotated by the identified angle of rotation; and producing an image of the patient anatomy with the artifact moved out of the area of interest using the second image data.

2. The method of claim 1, wherein the patient anatomy includes the patient's skull.

3. The method of claim 1, wherein the CT scan includes cone beam CT flat panel detection which captures a plurality of 2-D projection images at incremental angles around the patient anatomy.

4. The method of claim 1, further including rotating the component of the image control system by the identified angle of rotation.

5. The method of claim 4, wherein rotating the component includes transmitting an instruction to a rotation system and rotating the component through a rotating element at a pivot point.

6. The method of claim 5, wherein the rotating element includes a motor.

7. The method of claim 4, wherein the component is a table configured to be rotated about a pivot point within a horizontal plane.

8. The method of claim 4, wherein the component is a c-arm of an imaging system configured to be rotated about a vertical axis.

9. The method of claim 1, further including combining the image data and the second image data to produce a composite image of the patient anatomy without the artifact.

10. The method of claim 1, wherein receiving the location of the area of interest includes receiving input from a practitioner through a GUI.

11. The method of claim 1, wherein receiving the location of the area of interest includes identifying, by the processor, the area of interest through image analysis and stored information.

12. An image control system, comprising:
a table including a surface for supporting a patient;
a head frame including at least one pin configured to be secured to a patient anatomy in order to immobilize the patient anatomy relative to the table;
an imaging system configured to perform a CT scan in order to produce an image of the patient anatomy using x-rays, the image including an area of interest and an artifact caused by the at least one pin;
a control system configured to determine a trajectory of the at least one pin based on the image produced by the imaging system and identify an angle of rotation which will rotate the artifact out of the area of interest based on the trajectory of the one or more pins;
a rotation system configured to rotate the at least one pin relative to a path of the x-rays in order to adjust or alter a position of an artifact associated with the at least one pin in a subsequent image of the patient anatomy such that the artifact does not block the area of interest.

13. The image control system of claim 12, wherein the patient anatomy includes the patient's skull.

14. The image control system of claim 12, wherein the rotation system includes a pivot point on the table and a rotating element configured to rotate the table about a vertical axis with the surface remaining in a common plane.

15. The image control system of claim 14, wherein the head frame rotates with the table in order to rotate the at least one pin about a vertical axis while the imaging system remains stationary.

16. The image control system of claim 12, wherein the imaging system includes a transmission element and an opposing detection element which are connected by a C-arm and configured to rotate about a horizontal axis in order to collect image data at incremental angles around the patient anatomy.

17. The image control system of claim 16, wherein the rotation system includes a pivot point on the C-arm and a rotating element configured to rotate the C-arm about a vertical axis while the at least one pin remains stationary.

18. The image control system of claim 12, further comprising a control system having a processor configured to receive image data from a first CT scan of the patient anatomy and determine an angle of rotation for moving the artifact out of an area of interest in the image of the patient anatomy.

19. The image control system of claim 18, wherein the processor is further configured to provide an instruction to the rotation system to rotate at least one of the table, head frame, or the imaging system by the angle of rotation.

20. A computer-implemented method for producing an image of a patient anatomy using x-ray through an image control system comprising a table, a head frame including at least one pin configured to be secured to a patient's skull, an imaging system comprising a transmission element and a detecting element connected by a C-arm, a rotation system including a rotating element configured to rotate at least one of the table, head frame, or the C-arm about a vertical axis, and a control system comprising a processor, the method comprising:
receiving image data associated with a CT scan of the patient's skull while the patient's skull is immobilized by the at least one pin, the image data comprising an area of interest which is masked by an artifact associated with the at least one pin;
determining, by the processor, a trajectory of the at least one pin based on the image data;
identifying, by the processor, an angle of rotation which will rotate the artifact out of the area of interest based on the trajectory of the at least one pin;
providing an instruction to the rotating element to rotate the at least one of the table, the head frame, or the C-arm about the vertical axis by the angle of rotation;
receiving second image data associated with a second CT scan of the patient anatomy after the rotation is completed; and
producing an image of the patient anatomy with the artifact moved out of the area of interest using the second image data.

* * * * *